(12) United States Patent
Sato et al.

(10) Patent No.: US 6,926,058 B2
(45) Date of Patent: Aug. 9, 2005

(54) SAMPLE PRETREATMENT SYSTEM (75) Inventors: Kei Sato, Tokyo (JP); Hideaki Kubonoya, Tokyo (JP)

(73) Assignee: Aloka Co., Ltd. (JP)

( * ) Notice: Subject to any disclaimer, the term of this patent is extended or adjusted under 35 U.S.C. 154(b) by 304 days.

(21) Appl. No.: 10/400,153

(22) Filed: Mar. 25, 2003

(65) Prior Publication Data

US 2003/0215362 A1 Nov. 20, 2003

(30) Foreign Application Priority Data

Mar. 29, 2002 (JP) ........................................ 2002-095702

(51) Int. Cl.⁷ .............................. B65C 3/08; B65C 3/16
(52) U.S. Cl. ....................... 156/556; 156/558; 156/566; 156/DIG. 8; 156/DIG. 13; 156/539
(58) Field of Search ................................. 156/391, 489, 156/538–542, 556, 558, 566, 567, DIG. 5, DIG. 6, DIG. 7, DIG. 8, DIG. 9, DIG. 10, DIG. 11, DIG. 12, DIG. 13, DIG. 24, DIG. 27, DIG. 37, DIG. 40

(56) References Cited

U.S. PATENT DOCUMENTS

| 3,736,208 | A | * | 5/1973 | Kraft et al. .................. 156/541 |
| 3,956,983 | A | * | 5/1976 | Dittrich et al. ................. 101/6 |
| 4,798,095 | A | | 1/1989 | Itoh |
| 5,688,361 | A | * | 11/1997 | Itoh ........................... 156/362 |
| 5,893,263 | A | | 4/1999 | Matsumoto et al. |
| 6,325,129 | B1 | * | 12/2001 | Wright et al. ............... 156/538 |
| 6,599,476 | B1 | * | 7/2003 | Watson et al. ................ 422/63 |
| 2002/0001542 | A1 | | 1/2002 | Itoh |

FOREIGN PATENT DOCUMENTS

| EP | 0642024 A1 | 3/1995 | .......... G01N/35/00 |
| JP | 07309316 A | * 11/1995 | ............. B65C/3/12 |
| JP | 10007119 A | * 1/1998 | ............. B65C/9/34 |
| JP | 10-024911 | 1/1998 | ............. B65C/3/02 |
| JP | 10024911 | 1/1998 | ............. B65C/3/04 |
| JP | 10139023 A | * 5/1998 | ............. B65C/3/02 |
| JP | 2000266755 | 9/2000 | .......... G01N/35/02 |
| JP | 2001225820 A | * 8/2001 | ............. B65C/3/16 |
| JP | 2003104339 | 4/2003 | ............. B65C/3/16 |
| WO | WO99/28724 | 6/1999 | ............ G01N/1/00 |

* cited by examiner

Primary Examiner—Sue A. Purvis
(74) Attorney, Agent, or Firm—Marger Johnson & McCollom, P.C.

(57) ABSTRACT

A sample pretreatment system is equipped with a label sticking apparatus for sticking labels on containers. In this system, a manipulator 72 grasps and holds a container before label sticking from the pipetting apparatus to convey it to a receiving position on the line L—L along with the raising/lowering path of a container holding device 82. The container holding device 82 is raised by the raising/lowering mechanism 86 to be positioned at a receiving position in a complexly opened state. After receiving the container, the container holding device 82 is lowered, and then the container holding device 82 carries out the closing operation according to the lowering motion, thereby enabling to hold the container reliably irrespective of the diameter of the container. At the label sticking position which is set at a lower position, a label is stuck to the container. Then, the container holding device 82 is raised, and the transfer mechanism 83 rotates the labeled container which has been raised to the buffer position on the line B—B for a temporally evacuation. This sample pretreatment system makes it possible to handle containers of various diameters and carry out efficient container conveyance and label sticking with a simple structure.

4 Claims, 5 Drawing Sheets

SAMPLE PRETREATMENT SYSTEM

BACKGROUND OF THE INVENTION

1. Field of the Invention

The present invention is related to a sample pretreatment system, and in particular to a sample pretreatment system equipped with a label sticking apparatus for sticking labels on containers.

2. Description of the Prior Art

In a sample pretreatment system which is equipped with an automatic pipetting apparatus for subdividing (pipetting) a source sample such as a blood sample or the like into a plurality of secondary samples, a label sticking apparatus is used to stick a bar code label or the like on each sample container (test tube, blood sample vial, etc.) in order to prevent the wrong sample from being taken or the like. In Japanese Laid-Open Patent Publication No. HEI 10-24911, there is disclosed a label sticking apparatus which enables to carry out high-speed label sticking. This label sticking apparatus is provided with a main position having an insertion hole for holding a secondary sample container onto which a label is to be stuck, and an adjacent buffer position having a buffer hole for holding a secondary sample container on which a label has been stuck.

In the prior art label sticking apparatus described above, because a secondary sample container is held in the insertion hole or the buffer hole, the following problems occur when the container size is varied.

Namely, the containers have various sizes in accordance with the different kinds of tests to be carried out on the sample inside the container. For example, there are many cases where containers having a diameter in the range of 11 mm~17 mm are used. Accordingly, when the insertion hole and the buffer hole are set to match a particular external dimension of a container (e.g., an outer diameter of 15 mm), it becomes impossible to insert a larger container (e.g., a container having an outer diameter of 17 nm). On the other hand, when a smaller container (e.g., a container having an outer diameter of 12 mm) is inserted, there will be significant rattling, and this will hinder the label sticking operation.

SUMMARY OF THE INVENTION

In view of the problems of the prior art described above. it is an object of the present invention to provide a sample pretreatment system having a simple structure which can properly handle containers having various diameters, and which makes it possible to efficiently carry out container conveyance and label sticking operation.

In order to achieve the above-mentioned object, the present invention is directed to a sample pretreatment system equipped with a pipetting apparatus for pipettlng a sample to containers, a label sticking apparatus for sticking a label to each container, and a container conveying apparatus for conveying the containers. The label sticking apparatus comprises: a container holding device for holding the container with an elastic holding force, the holding device being adapted to open and close; a raising/lowering mechanism for raising and lowering the container holding device along a raising/lowering path, the raising/lowering mechanism positioning the container holding device at a container receiving position which is set at an upper position when receiving the container, positioning the container holding device at a label sticking position by lowering the container holding device after receiving the container, and then raising the container holding device upwardly from the label sticking position after the label has been stuck on the container; an opening/closing control mechanism for mechanically controlling opening and closing operations of the container holding device so that the container holding device is in a completely opened state at the receiving position and so that the container holding device carries out the closing operation according to the lowering motion of the container holding device from the receiving position to hold the container: a label sticking apparatus for sticking a label onto the container held by the container holding device at the sticking position: and a transfer mechanism for receiving the container to which the label has been stuck from the container holding device which has been raised after sticking the label and then conveying the container to which the label has been stuck horizontally to position the labeled container at a buffer position. The container conveying apparatus is constructed so that the container conveying apparatus carries out feeding conveyance of a container before label sticking from the pipetting apparatus to the container holding device positioned at the receiving position in an outward conveyance and carries out returning conveyance of the container to which the label has been stuck and which is positioned at the buffer position to the pipetting apparatus in a returned conveyance.

According to the sample pretreatment system having the structure as described above, the container holding device which can be opened and closed for holding the container receives the container before label sticking from the container conveying apparatus in a completely opened state at the container receiving position which is set at the upper position on the raising/lowering path. Therefore, this sample pretreatment system can deal with containers having large diameters, that is this system can handle containers having diameters up to the maximum diameter determined by the system. Further, in this system, the container holding device is lowered along the raising/lowering path by the raising/lowering mechanism so that the container holding device is operated to be closed to hold the container by the opening/closing control mechanism according to the lowering motion of the container holding device. Therefore, in this system, a container having a larger diameter is held at the slightly lowered position, and a container having a smaller diameter is held at a further lowered position. Namely, containers having various diameters are reliably held according to their diameters. Further, since the label sticking operation is carried out at the lowest position, label sticking can be carried out for the containers having various diameters. Furthermore, since in this system, the container to which the label has been stuck is transferred to the buffer position for a temporary evacuation, and the container conveying apparatus carries out feeding conveyance of a container before label sticking in an outward conveyance thereof and carries out returning conveyance of the container to which the label has been stuck in a returned conveyance thereof, thereby enabling to carry out efficient container conveyance and label sticking.

In the present invention, it is preferred that the raising/lowering mechanism is operated to position the container holding device at the transfer position by raising the container holding device after the label has been stuck onto the container and the opening/closing control mechanism is operated so that the container holding device is in a partially opened state before the completely opened state.

If a container is transferred to the transfer mechanism in a completely opened state of the container holding device irrespective of the diameter of the container, rattling necessarily occurs and significant rattling will occur in the case of the container having a small diameter. On the other hand however, if the container is transferred in the partially opened state before the completely opened state, the rattling of the container in the container holding device can be made small or zero.

Further, in the present invention, it is preferred that the transfer position is set depending on the diameter of the container to be transferred. According to this, the condition of the container holding device at the transferring of the container can be made appropriately depending on the diameter of the container. In this case, the diameter of the container may be measured by a sensor. Further, in the case where the diameter is already known such data of the diameter may be inputted into the control section in advance.

Another aspect of the present invention is directed to a sample pretreatment system equipped with a pipetting apparatus for pipetting a sample to containers, a lable sticking apparatus for sticking a label to each container, and a container conveying apparatus for conveying the containers. The label sticking apparatus comprises; a container holding device for holding the container with an erastic holding force, the holding device being adapted to open and close; a raising/lowering mechanism for raising and lowering the container holding device along a raising/lowering path, the raising/lowering mechanism positioning the container holding device at a container receiving position which is set at an upper position when receiving the container, positioning the container holding device at a label sticking position by lowering the container holding device after receiving the container, and then raising the container holding device upwardly from the label sticking position after the label has been stuck onto the container; a control mechanism for mechanically controlling opening and closing operations of the container holding device so that the container holding device is in a completely opened state at the receiving position and so that the container holding device carries out the closing operation according to the lowering motion of the container holding device from the receiving position to hold the container: a label sticking apparatus for sticking a label onto the contain held by the container holding device at the sticking position: and a transfer mechanism for transferring the container before label sticking positioned at a buffer position to the container holding device at the receiving position by transferring the container horizontally. The container conveying apparatus is constructed so that the container conveying apparatus carries out feeding conveyance of a container before label sticking from the pipetting apparatus to the buffer position in an outward conveyance and carries out returning conveyance of the container by receiving the container to which the label has been stuck from the container holding device which has been raised after sticking the label.

According to the sample pretreatment system having the structure as described above, the buffer position is provided before the label sticking operation is carried out, and the container holding device which can be opened and closed for holding the container receives the container before label sticking from the transfer mechanism at the container receiving position which is set at the upper position on the raising/lowering path. Then, the container holding device is lowered along the raising/lowering path by the raising/lowering mechanism so that the container holding device is operated to be closed to hold the container by the opening/closing control mechanism according to the lowering motion of the container holding device. Thereafter, the label sticking operation is carried out at the lowest position. Therefore, label sticking can be carried out for the containers having various diameters. Further, since in this system, the container conveying apparatus carries out feeding conveyance of a container before label sticking in an outward conveyance thereof and carries out returning conveyance of the container to which the label has been stuck in a returned conveyance thereof, thereby enabling to carry out efficient container conveyance and label sticking.

The above and other objects, structures and advantages of the present invention will be more apparent when the following detailed description of the embodiments is considered in conjunction with the accompanied drawings.

DETAILED DESCRIPTION OF THE PREFERRED EMBODIMENTS

The preferred embodiments of the present invention will now be described in detail with reference to the drawings.

Figure 1:
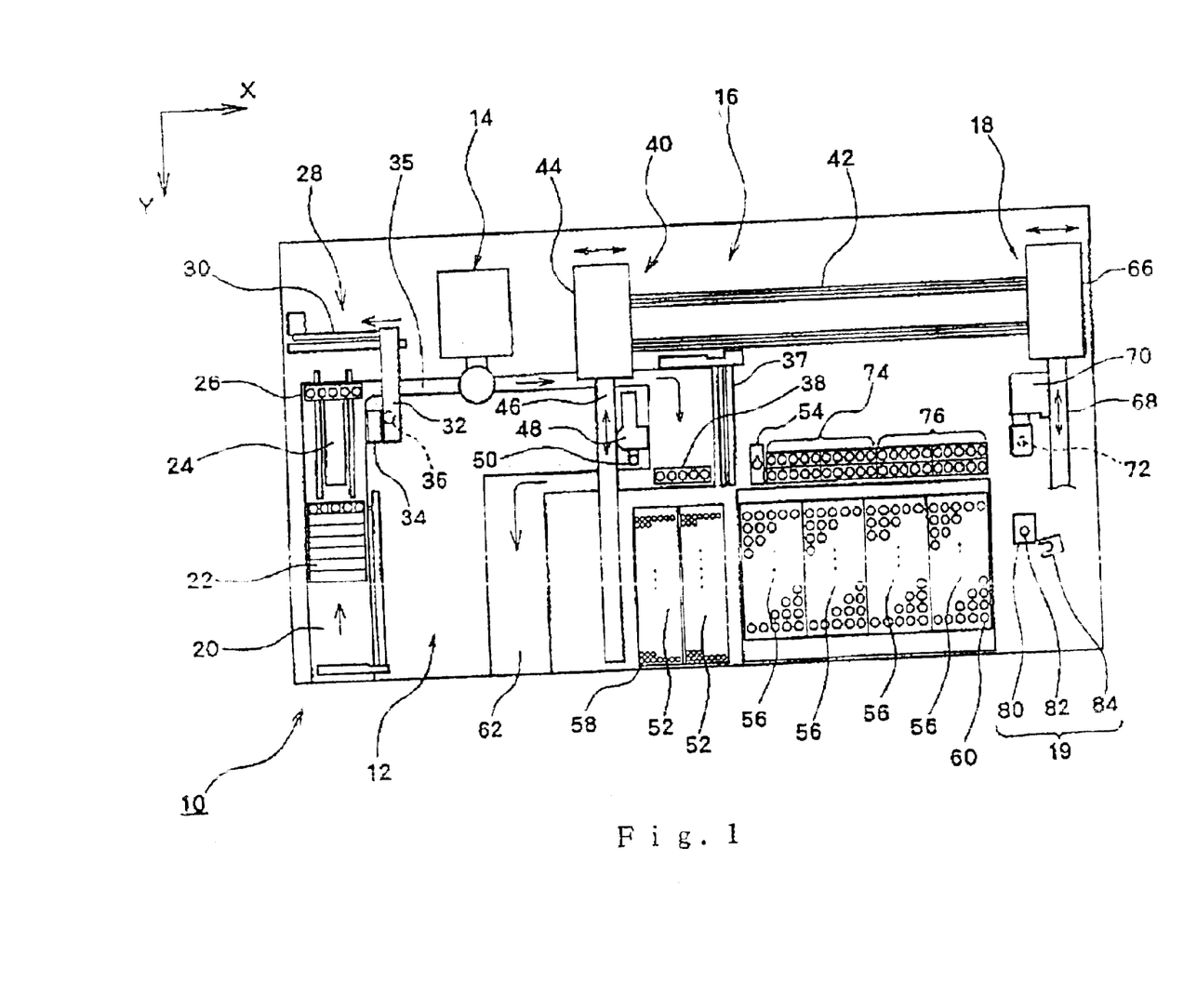
FIG. 1 is a top view which shows the overall structure of one embodiment of a sample pretreatment system according to the present invention.

FIG. 1 is a top view which shows the overall structure of a sample pretreatment system 10. The sample pretreatment system 10 is equipped with a source sample rack conveying apparatus 12 which sequentially conveys source sample racks in which source sample containers are arranged to a pipetting apparatus, a cap opening unit 14 which removes the cap of a source sample container for enabling pipetting operation to be carried out, a pipetting apparatus 16 which uses a nozzle and a pipetting pump to subdivide the source sample in the source sample container to a plurality of secondary sample containers arranged in a secondary sample rack, a container conveying apparatus 18 which conveys containers, and a label sticking apparatus 19 which sticks labels on containers The control of all the operations of the sample pretreatment system 10 is carried out by a control section not shown in the drawings, and all the operations of the sample pretreatment system 10 are displayed on a display not shown in the drawings. The X-axis direction and the Y-axis direction are shown in FIG. 1 to make it easy to understand the conveying direction of the source sample rack and the like. The Z-axis direction is orthogonal to the plane of the paper.

Source sample racks 22 are placed in a rack receiving portion 20 of the source sample rack conveying apparatus 12 by a manual operation or by the use of a separate apparatus. The source sample racks 22 are placed in the rack receiving portion 20 so that the longitudinal direction of each rack is directed to the X-axis direction. The placed source sample racks 22 are fed forward along a feeding path in the Y-axis direction by a feeding mechanism, A rack separation mechanism 24 provided at a predetermined separation position separates the head source sample rack 22 from the placed source sample racks 22. The separated source sample rack 22 is moved by the moving mechanism in the Y-axis direction to a label reading position 26, and is set at such position.

The source sample rack conveying apparatus 12 has a detection unit conveying mechanism 28 which includes a moving arm 32 which can move along a first guide rail 30 in the X-axis direction. The moving arm 32 extends over the top of the source sample rack 22 set at the label reading position 26, and a label reader 34 and a container presence/absence detection sensor 36 are arranged so as to hang downward at the tip portion thereof. The label reader 34 and the container presence/absence detection sensor 36 are arranged to face the side surface of the source sample rack 22 which is opposite to the side surface of the source sample rack 22 facing to the first guide rail 30. A bar code reader can be used for the label reader 34, for example, and a reflection-type optical sensor can be used for the container presence/absence sensor 36, for example.

In the structure described above, by controlling the detection unit conveying mechanism 28, the moving arm 32 can be moved in the X-axis direction so that the label reader 34 and the container presence/absence sensor 36 can be moved in the X-axis direction, namely, in the direction along which the containers are arranged in the source sample rack. I this way, the detection of the presence or absence of each container is sequentially carried out by the container presence/absence sensor 36, and the bar code of the label stuck on each container is also sequentially read out by the label reader 34. The read out data is transmitted to a control section not shown in the drawings.

The source sample rack 22 having the containers of which labels have been readout by the label reader 34 is then conveyed to the position of the cap opening unit 14 by a belt line 35 which moves in the X-axis direction. The cap opening unit 14 carries out a cap opening operation on each container. Namely, because a container such as a blood sample vial is provided with a rubber cap or the like to prevent contamination, the cap is removed by the cap opening unit 14 before pipetting operation.

The source sample rack 22 that has undergone the cap opening operation is conveyed further along the X-axis direction by the belt line 35, and then this source sample rack 22 is moved in the Y-axis direction and set at a pipetting position 38 by a setting mechanism 37.

Next, a description will be made with regard to the pipetting apparatus 16. The pipetting apparatus 16 includes a nozzle conveying mechanism 40 which can convey the nozzle freely in the three axial directions of the X-axis, the Y-axis and the Z-axis. The nozzle conveying mechanism 40 is equipped with two second guide rails 42 arranged in the X-axis direction, a first base 44 which can move in the X-axis direction on the second guide rails 42, a first Y-axis arm 46 which is integrally formed with the first base 44 to extend in the Y-axis direction, and a nozzle pedestal 48 which can move in the X-axis direction along the first Y-axis arm 46, wherein a nozzle 50 is provided on the nozzle pedestal 48. The nozzle 50 is movable in the Z-axis direction with respect to the nozzle pedestal 48. The nozzle 50 is constructed from a nozzle base and a nozzle tip which is removably attached to the nozzle base. Further, the nozzle pedestal 48 is also provided with a pipetting pump connected to the nozzle 50 with a piping tube or the like. Of course, the pipetting pump may be separately arranged outside the nozzle pedestal 48.

Further, the above-described pipetting position 38 is established inside the space in which the nozzle can be conveyed by the nozzle conveying mechanism 40, and a plurality of tip racks 52, a tip remover 54 and a plurality of secondary sample racks 56 are also provided inside that space.

Each of the tip racks 52 holds a plurality of rows of unused nozzle tips 58 arranged so that the tip head openings in which the nozzle base is inserted are facing upward.

Namely, the unused nozzle tips 58 are arranged with their tip head openings facing upward to enable the unused nozzle tips 58 to fit onto the nozzle base when the nozzle base is lowered in the Z-axis direction. It is possible to provide a plurality of tip racks 52 according to the treatment capacity of the system.

The tip remover 54 hooks onto each of the used nozzle tips to remove it from the nozzle base. A tip disposal container not shown in the drawings is arranged directly below the tip remover 54, and the removed used nozzle tips are disposed of by being dropped into the tip disposal container.

In each of the secondary sample racks 56, there are provided a plurality of secondary sample containers 60 which are arranged in rows. When the system begins operation or when the secondary sample racks are replaced, a plurality of secondary sample racks 56 holding only unused secondary sample containers 60 are set at a secondary sample rack arranging location.

The pipetting sequence is carried out as follows under the control of a control section not shown in the drawings. First, operations start in a state in which a nozzle tip is not attached to the nozzle base. Accordingly, the nozzle conveying mechanism 40 is operated to move the nozzle base in a horizontal direction to a position directly above the tip rack 52. Then, the nozzle base is lowered toward the tip head opening of one unused nozzle tip 58 selected from the group of unused nozzle tips 58 until the nozzle base is pushed into the tip head opening of such selected unused nozzle tip 58, whereby the nozzle 50 is formed. Next, the nozzle 50 is raised to a prescribed height, and then the nozzle 50 is moved in a horizontal direction to a position directly above a source sample container containing a source sample to be pipetted at the pipetting position 38. At this point, preparation for the pipetting operation is setup.

Next, the nozzle 50 is lowered, and then a predetermined amount of the source sample is aspirated inside the nozzle tip by operating and controlling the pipetting pump. For example, when pipetting to three secondary sample containers, the predetermined amount would be the total amount necessary for creating three secondary samples therefor.

Next, with the predetermined amount of source sample being held inside the nozzle tip, the nozzle 50 is raised to a predetermined height, and then the nozzle 50 is moved so that it is positioned directly above a secondary sample container 60 to which the source sample is to be pipetted. Then, the nozzle 50 is lowered at this position, and a predetermined amount of the source sample held inside the nozzle is dispensed by operating and controlling the pipetting pump. This sequence is then repeated to pipet (subdivide) the source sample from one source sample container to a predetermined number of unused secondary sample containers.

When the pipetting operations for the source sample in one source sample container are completed, the nozzle 50 is moved in a horizontal direction, and the nozzle 50 is positioned directly above the tip remover 54. Then, the nozzle 50 is lowered, and after the used nozzle tip is hooked by the tip remover 54, the nozzle 50 is raised to a predetermined height, whereby the used tip is removed from the nozzle base and falls into the tip disposal container arranged directly below the tip remover 54. Next, a new unused nozzle tip is attached to the nozzle base as described above, and the same sequence for pipetting a source sample from the next source sample container is carried out repeatedly.

When predetermined pipetting operations have been carried out for all the source sample containers arranged in one source sample rack, such source sample rack is conveyed along a conveying path and sent to a discharge section 62, and then the source sample rack is carried to the outside automatically or manually.

Next, a description will be given for the container conveying apparatus 18. The container conveying apparatus 18 is a mechanism which freely conveys containers held by a manipulator in the three axial directions of the X-axis, the Y-axis and the Z-axis. The container conveying apparatus 18 is equipped with the two second guide rails 42 arranged in the X-axis direction which are also utilized by the nozzle conveying mechanism 40, a second base 66 which can move in the X-axis direction on the second guide rails 42, a second Y-axis arm 68 which is integrally formed with the second base 66 to extend in the Y-axis direction, and a manipulator pedestal 70 which can move in the X-axis direction along the second Y-axis arm 68, wherein a manipulator 72 is provided on the manipulator pedestal 70, The manipulator 72 is movable in the Z-axis direction with respect to the manipulator pedestal 70.

Because the second guide rails 42 are utilized by both the container conveying apparatus 18 and the nozzle conveying mechanism 40, the area where the manipulator 72 can be moved covers a wide area up to the source sample rack at the pipetting position. Therefore, by using the manipulator 72, it is possible to convey containers to an abnormal source sample elimination area 74, a secondary sample container placing area 76 for urgent samples and the label sticking apparatus 19 which are provided inside the area of such movement, respectively.

The abnormal source sample elimination area 74 is an area for receiving a source sample container recognized as an abnormal source sample. The cases where a source sample is recognized as an abnormal source sample can include cap opening mistakes, pipetting mistakes and the like in addition to the case where there are label reading errors or errors in the recognition of the presence or absence of a container at the label reading position 26, for example. The source sample container recognized as containing an abnormal source sample is temporarily sent to the pipetting position 38. Then, by operating the container conveying apparatus 18 in accordance with instructions from a control apparatus not shown in the drawings, the manipulator 72 is moved directly above the abnormal source sample container at the pipetting position 38, and after being lowered to grasp the abnormal source sample container, the manipulator 72 is raised to a predetermined height and then moved directly above the abnormal source sample elimination area 74. Then, the manipulator 72 is lowered at the position of a predetermined container holding location inside the abnormal source sample elimination area 74, and the grip is released to store the abnormal source sample container at such a location.

Further, the secondary sample container placing area 76 for urgent samples is provided for receiving secondary sample containers in which the urgent samples have been pipetted from the urgent source sample containers. Before receiving the secondary sample containers, there is no container in this area 76. When a source sample container containing an urgent source sample is put in the rack receiving portion 20 of the source sample rack conveying apparatus 12, the manipulator 72 grasps required secondary sample containers 60 from the secondary sample rack 56 and conveys them to the label sticking apparatus 19 based on the data of such an urgent source sample. After the label sticking apparatus 19 sticks predetermined labels on the secondary sample containers 60, the manipulator 72 conveys the secondary sample containers 60 from the label sticking apparatus 19 to the secondary container receiving area 76 for urgent samples. Then, the pipetting apparatus 16 carries out pipetting operation for the urgent source sample from the urgent source sample container set at the pipetting position to the secondary sample containers in the secondary sample container placing area 76 for urgent samples.

In addition to this method, it is also possible to carry out pipetting operation for an urgent source sample from an urgent source sample container set at the pipetting position 38 according to the normal sequence to predetermined secondary sample containers in the secondary sample rack 56, and then using the manipulator 72, the secondary sample containers to which the urgent sample have been pipetted can be conveyed to the secondary sample placing area 76 for urgent samples.

Next, a description will be made with regard to the label sticking apparatus 19. The label sticking apparatus 19 is equipped with a label sticking device 80 and a container holding device 82, and cooperates with a transfer mechanism 84 for conveying containers. The label sticking device 80 prepares predetermined labels which will be stuck to secondary sample containers, and sticks a label to a secondary sample container received by the container holding device 82. In the label sticking process, data of the source sample container obtained at the label reading position 26 are transmitted so that this process can be carried out in parallel with the pipetting operation.

By repeatedly carrying out the series of the processes described above, it is possible to carry out pipetting of a source sample and label sticking efficiently.

Figure 2:
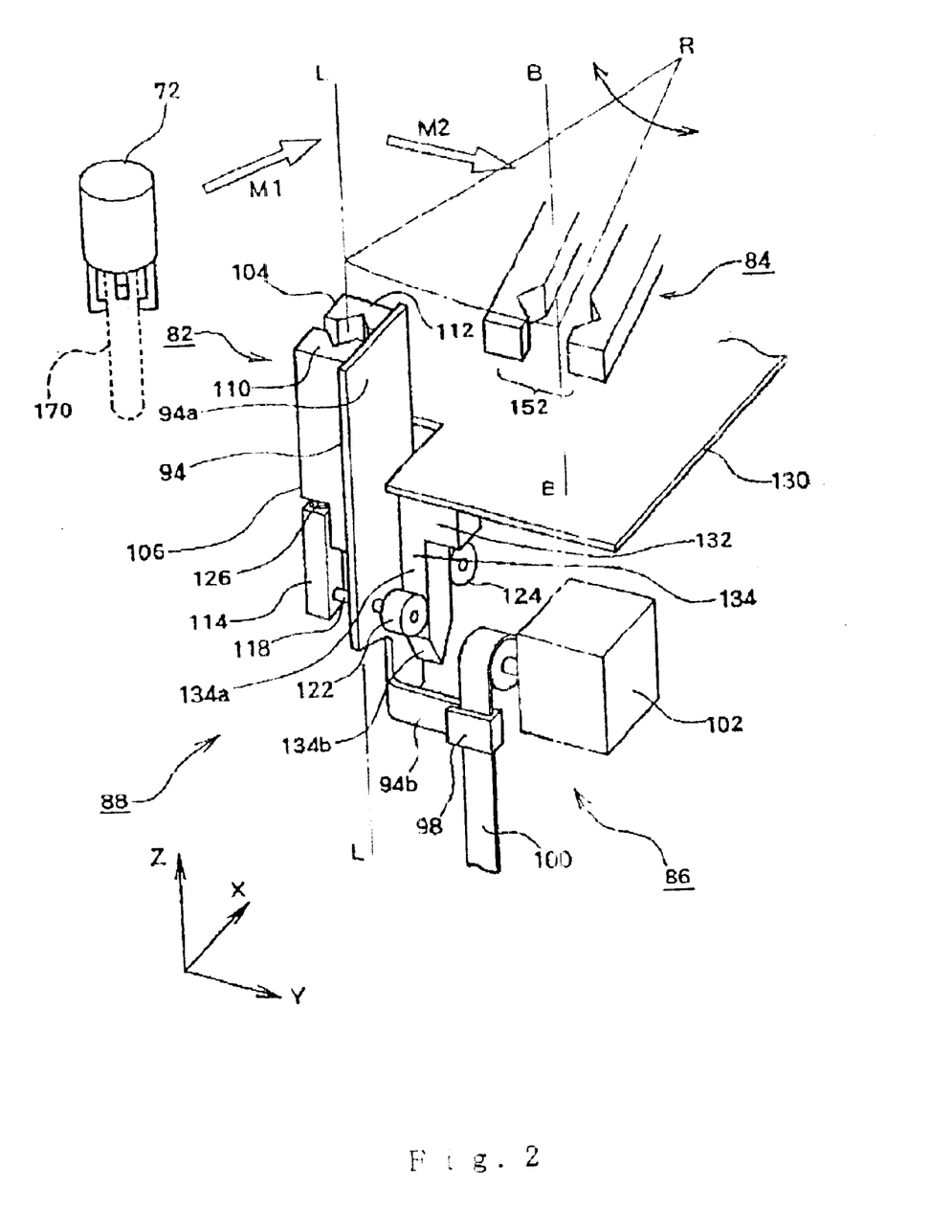
FIG. 2 is a perspective view which shows a container holding device and a conveying mechanism of the embodiment of the sample pretreatment system according to the present invention.

FIG. 2 shows the container holding device 82, the transfer mechanism 84, a raising/lowering mechanism 86 which raises and lowers the container holding device 82, and an opening/closing control mechanism 88 which controls the opening and closing of the container holding device 82 of the label sticking apparatus 19. In this regard, it is to be noted that the X-axis, the Y-axis and the Z-axis which are the same as those of FIG. 1 are also shown in this drawing.

In FIG. 2, the movable portions of the container holding device 82 are mounted to a raising/lowering plate 94 which is a part of the raising/lowering mechanism 86, and can be raised and lowered in the Z-axis direction by a guide in the Z-axis direction not shown in the drawings. The direction of the raising/lowering path of the container holding device 82 is shown by the line L—L. The raising/lowering plate 94 is formed from a vertical plate portion 94*a* and a mounting plate portion 94*b* which is formed by bending a lower narrow width portion of the vertical plate portion 94*a* at a right angle in the horizontal direction. The tip of the mounting plate portion 94*b* is folded to form a belt fixing portion 98 in which a belt 100 extending in the Z-axis direction is held to be fixed. One end of the belt 100 is wrapped around a drive roller provided on the output shaft of a raising/ lowering drive apparatus 102. For the raising/lowering drive apparatus 102, a step motor or the like may be used.

The raising/lowering plate 94, the belt fixing portion 98, the belt 100 and the raising/lowering drive apparatus 102 constitute the raising/lowering mechanism 86. Namely, when the drive roller is rotated in a stepwise manner by controlling the driving of the raising/lowering drive apparatus 102, the belt 100 wrapped around the drive roller is raised or lowered in the Z-axis direction, whereby the belt fixing portion 98 fixed to the belt 100 is also raised or lowered in the Z-axis direction. By operating this raising/lowering mechanism 86 in this manner, the container holding device 82 and the like are raised or lowered.

The container holding device 82 includes a pair of arm members 104, 106 which cross at an intermediate point. The upper portions of the pair of arm members 104, 106 form a pair of container holding members 110, 112 having V-shaped grooves formed therein which extend in the Z-axis direction to hold a container, and the opposite side lower portions of the container holding members 110, 112 form a pair of leg portions 114, 116 (the leg portion 116 is not shown in FIG. 2).

Further, in this container holding device 82, an elastic holding force is applied from a pair of compression springs 126, 128 (the compression spring 128 is not shown in FIG. 2) described later.

A pair of shafts 118, 120 (the shaft 120 is not shown in FIG. 2) are mounted to the tips of the pair of leg portions 114, 116, respectively. A pair of freely rotatable rollers 122, 124 are mounted to the pair of shafts 118, 120, respectively.

Further, in the crossing portion of the pair of arm members 104, 106, a pair of gaps are provided. For example, when giving a description with FIG. 2, a gap is provided between the bottom surface of the container holding member 110 and the top surface of the leg portion 114, and the compression spring 126 is arranged in such a gap. Although not shown in FIG. 2, the compression spring 128 is arranged in a gap provided between the bottom surface of the container holding member 112 and the top surface of the leg portion 116. A coil spring can be used as the compression spring, and it is also possible to use other elastic members in place of the compression spring, such as a plate spring, rubber member or the like.

The compression springs 126, 128 normally bias the pair of container holding members 110, 112 in the mutual closing direction. Namely, the compression springs 126, 128 give an elastic holding force to the container holding device 82. In addition, the pair of leg portions 114, 116 are also biased in the mutual closing direction. Accordingly, the pair of rollers 122, 124 are also biased in the closing direction via the pair of shafts 118, 120 so as to have the function of controlling the opening and closing of the container holding device 82. The container holding surfaces of the V-shaped grooves of the pair of container holding members 110, 112 may be provided with elastic members such as rubber members or the like.

A pushing and widening member 132 for widening the space between the pair of rollers 122, 124 is fixed to a fixed plate 130. The pushing and widening member 132 has a parallel surface portion having parallel surfaces 134*a* and a wedge-shaped portion provided in the lower side of the parallel surface portion and having inclined surfaces 134*b* tapered downwardly. the parallel surfaces 134*a*, 134, and the inclined surfaces 134*b*, 134*b* of the pushing and widening member 132 constitute a pair of rolling surfaces 134, 134 (only one rolling surface 134 is shown in FIG. 2) on which the pair of rollers 122, 124 are abutted with a pressing force. As described below, the pushing and widening member 132 and the pair of rollers 122, 124 constitute the opening/closing control mechanism 88 which mechanically controls the opening and closing of the container holding device 82 in accordance with the position of the container holding device 82 along the raising/lowering path.

Namely, the pair of rollers 122, 124 mounted to the raising/lowering plate 94 are raised or lowered in the Z-axis direction together with the container holding device 82. In accordance with such raising or lowering motion, the pair of rollers 122, 124 roll up or down on the pair of rolling surfaces 134, 134.

In accordance with the raising or lowering of the raising/lowering plate 94, the pair of container holding members 110, 112 move in the opening direction when the horizontal spacing between the pair of rollers 122, 124 is widened, and the pair of container holding members 110, 112 move in the closing direction when the horizontal spacing between the pair of rollers 122, 124 is narrowed.

Figure 3:
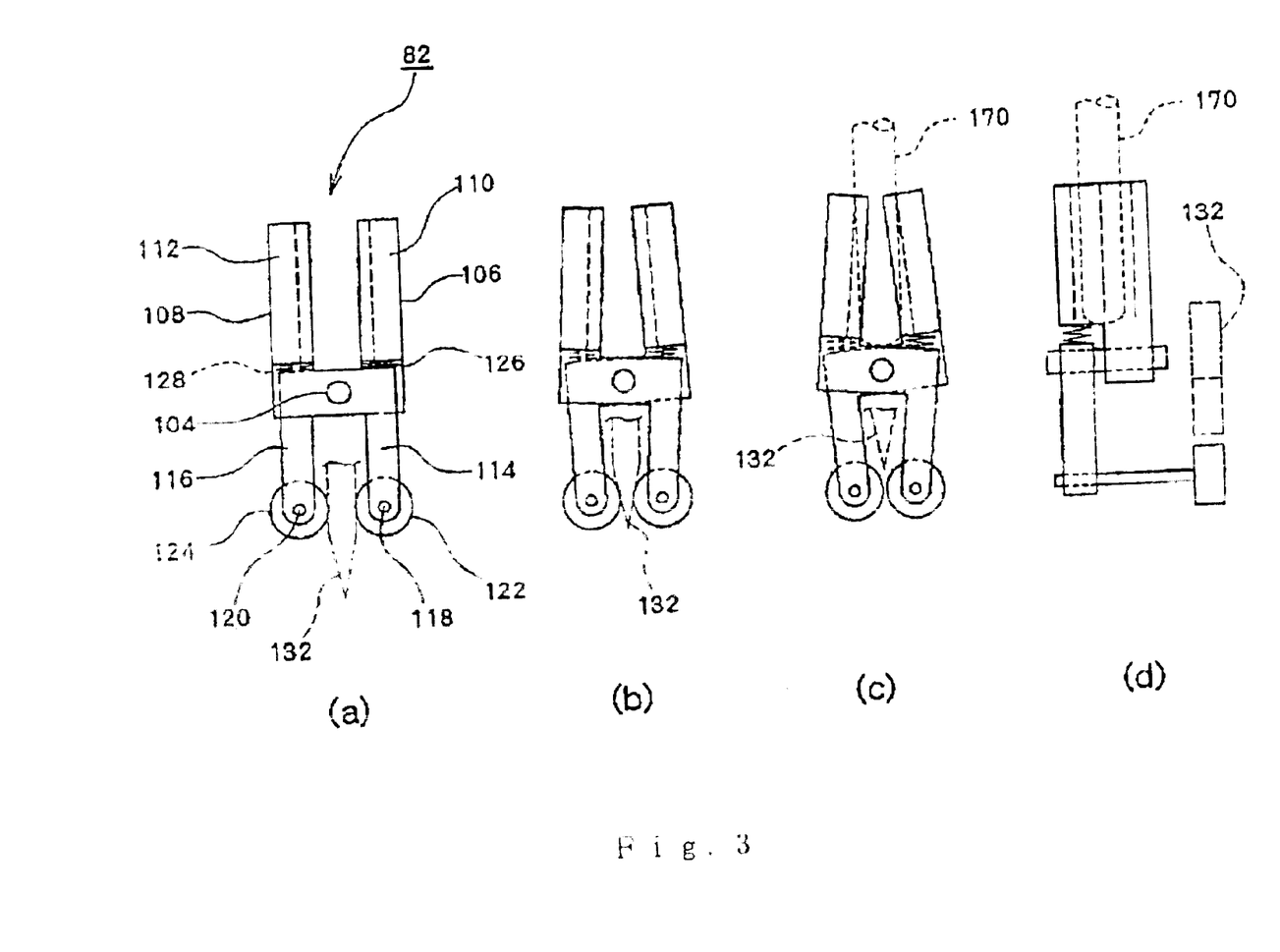
FIG. 3 is a schematic illustration for explaining the operations of the container holding device of the embodiment of the sample pretreatment system according to the present invention.

Using FIG. 3 as needed, a description will be given for the relationship between the opening and closing of the container holding members 110, 112 and the position of the container holding device 82 on the line L—L showing the direction of the raising/lowering path of the container holding device 82. FIG. 3(*a*) shows the state where the container holding device 82 is at an upper position. In this state, the horizontal gap between the pair of rollers 122, 124 is maximum, and the container holding device 82 is in an open state. At this time, the pair of rollers 122, 124 are widened outward to their maximum horizontal spacing by contact with the parallel surfaces 134*a*, 134*a* which form the widest horizontal portion of the pushing and widening member 132.

Next, when the raising/lowering plate 94 is lowered, the container holding device 82 is gradually closed in accordance with such lowering motion. This state is shown by FIG. 3(*b*). At this time, the pair of rollers 122, 124 roll down the tapered inclined surfaces 134*b*, 134*b* of the pushing and widening member 132.

Then, when the container holding device 82 is lowered further, the container holding device 82 holds a container 170 firmly. This state is shown by FIGS. 3(*c*) and 3(*d*). At this time, the rollers 122, 124 have completely rolled down and off the tapered inclined surfaces 134*b*, 134*b* of the pushing and widening member 132, and the pushing and widening member 132 no longer lies between the rollers 122, 124. In this state, however, because the degree of opening of the container holding device 82 is determined by the diameter of the container 170, a gap corresponding to such degree of opening remains between the pair of rollers 122, 124. In this way, the container holding device 82 can reliably hold not only large-diameter containers but also small-diameter containers.

Figure 4:
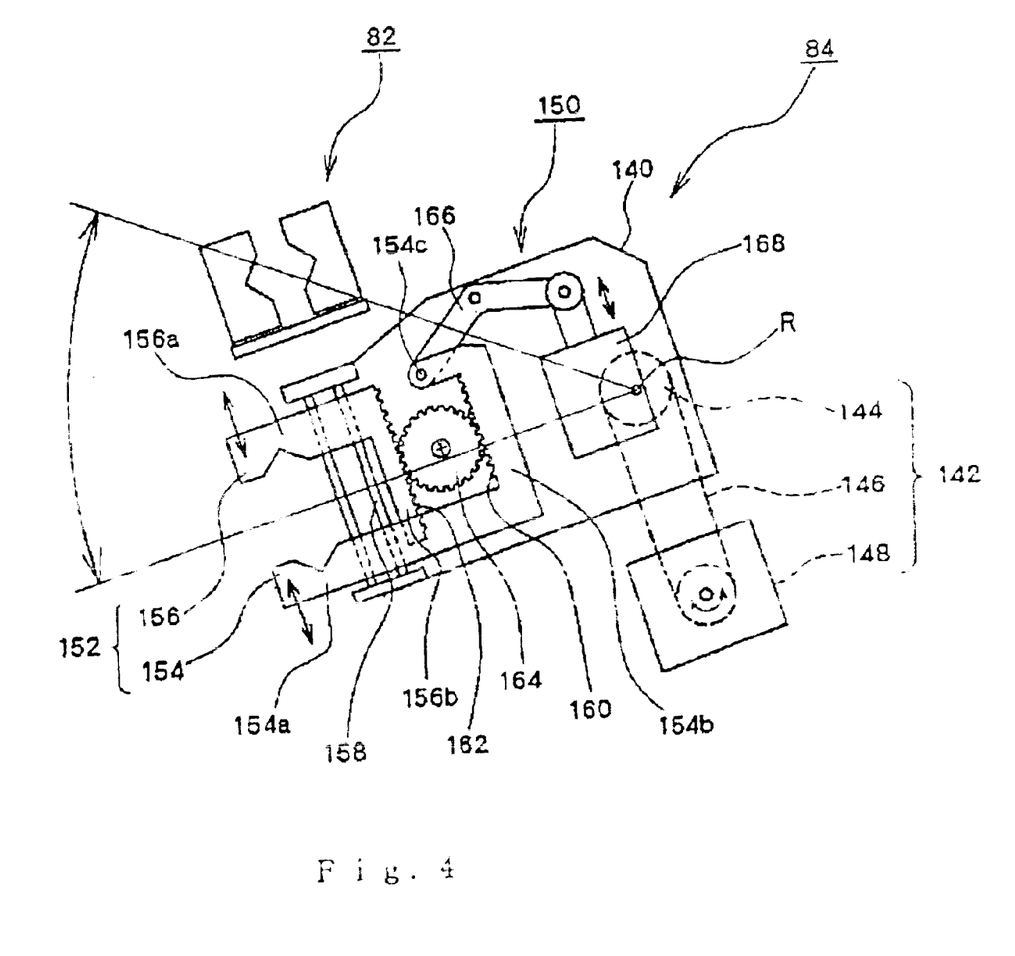
FIG. 4 is a top view which shows a transfer mechanism of the embodiment of the sample pretreatment system according to the present invention.

FIG. 4 is a detailed planar view of a portion of the transfer mechanism 84. The transfer mechanism 84 is equipped with a rotary plate 140 and a rotary drive mechanism 142. The rotary plate 140 rotates in the horizontal direction about the point R. The rotary mechanism 142 is equipped with a belt wheel 144 provided on the rotary plate 140, a belt 146 and a rotary drive device 148. The belt 146 is spanned over the belt wheel 144 and an output pulley provided on an output shaft of the rotary drive device 148. The rotary drive apparatus 148 can use a small-size motor. Accordingly, by controlling the driving of the rotary drive device 148, the belt 146 rotates the belt wheel 144, whereby the rotary plate 140 is rotated in the horizontal direction about the rotation point R.

An opening/closing mechanism 150 of a container clamping portion 152 is provided on the rotary plate 140. The opening/closing mechanism 150 is a mechanism which closes the container clamping portion 152 to clamp a container, and opens the container clamping portion 152 to release the clamping of a container. The container clamping portion 152 is equipped with a pair of container clamping members 154, 156 for clamping a container. Tip portions 154a, 156a of the pair of container clamping members 154, 156 have V-shaped grooves which are formed to extend in the Z-axis direction. The pair of container clamping members 154, 156 are opened and closed by the movement in the direction of the arrows shown in FIG. 4 along two guide shafts 158. When the clamping members 154, 156 completely open, it is possible to clamp containers having a diameter less than or equal to about 18 mm, for example. The pair of container clamping members 154, 156 also include rack portions 154b, 156b which have opposing rack surfaces 160, 162, and a pinion 164 is arranged to mesh with the opposing rack surfaces 160, 162. Further, the container clamping member 154 also includes a base portion 154c which is connected to a linear output shaft of a plunger 168 via a link mechanism 166.

Accordingly, by controlling the driving of the plunger 168, the plunger output shaft moves linearly, and this linear motion is converted to a symmetrical pivoting motion with respect to a fixed point in the middle of the link mechanism 166, whereby the base portion 154c of the container clamping member 154 moves linearly. This linear motion of the base portion 154c causes the container clamping member 154 to move along the guide shafts 158 in the direction of the arrows shown in FIG. 4. The movement of the container clamping member 154 is transmitted to the other container clamping member 156 as movement in the opposite direction via the pinion 164. For example, when the plunger 168 is driven so that the output shaft thereof protrudes outward, the tip portions 154a, 155a of the pair of container clamping members 154, 156 are opened, and when the plunger 168 is driven so that the output shaft thereof is pulled inside, the tip portions 154a, 156a of the pair of container clamping members 154, 156 are closed.

The holding and conveying of the container at the label sticking apparatus 19 will now be described with reference to FIG. 2. The manipulator 72 grasps a container (secondary sample container) before label sticking from a secondary sample rack, for example, and conveys such grasped container to a receiving position on the raising/lowering path line L—L of the container holding device 82. At the receiving position, the container holding device 82 receives the container 170 while in a completely open state, and after the container holding device 82 is closed to firmly grip the container 170, the container holding device 82 is lowered to the label sticking position, and then a label is stuck onto the container 170.

After the label sticking operation has been completed, the container holding device 82, which is still firmly holding the labeled container, is raised to a transfer position. At the transfer position, the container clamping portion 152 of the transfer mechanism 84 is in standby in a completely open state. At this point, the transfer mechanism 84 closes the container clamping portion 152 to hold the container with a clamping force, and then the container holding device 82 is lowered in order to evacuate the container holding device 82. In this way, the container is transferred from the container holding device 82 to the transfer mechanism 84. The transfer mechanism 84 rotates the transferred labeled container to the position of the line B—B (that is, the buffer position) in order to temporarily evacuate the container.

Hereinafter, a description will be made with regard to the case where the above-described sequence is carried out in a sequential manner. In such a case, when the manipulator 72 conveys a container (secondary sample container) before label sticking to the receiving position on the line L—L (as shown by the arrow M1 in FIG. 2), the previous labeled container is at the buffer position on the line B—B evacuated from the line L—L. Accordingly, the manipulator 72 conveys the container before label sticking to the receiving position on the line L—L, and then after the container holding device 82 receives the container before label sticking, the manipulator 72 is moved to the buffer position on the line B—B (as shown by the arrow M2 in FIG. 2). Then, the manipulator 72 grasps the previously labeled container clamped by the transfer mechanism 84. Next, the transfer mechanism 84 opens the container clamping portion 152, and the previously labeled container is transferred from the transfer mechanism 84 to the manipulator 72. Then, after the manipulator 72 is raised to a prescribed position, the labeled container is conveyed and returned to the secondary sample rack. In this way, because the manipulator 72 can bring the container before label sticking from the pipetting apparatus 16 to the receiving position on the outward conveyance, and then return the labeled container at the buffer position to the pipetting apparatus 16 on the return conveyance, an efficient conveyance is achieved.

Figure 5:
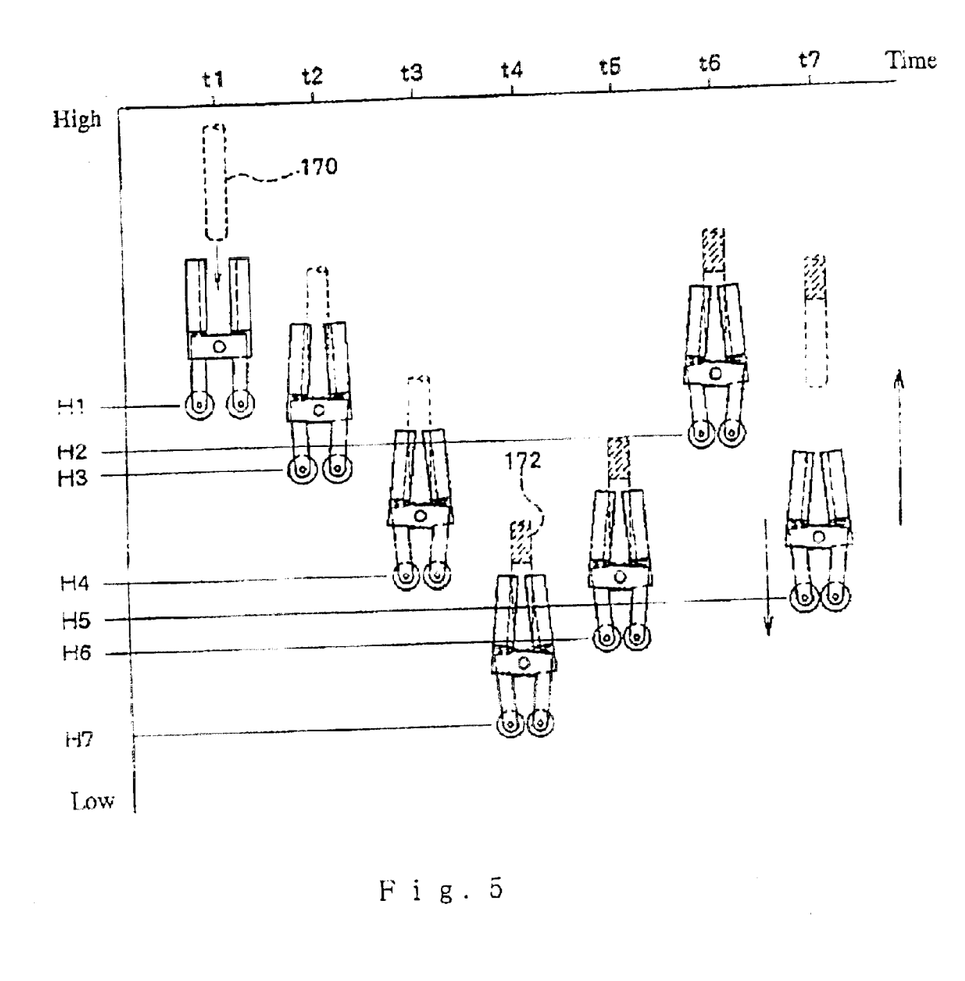
FIG. 5 is a schematic illustration for explaining the opening and closing operations of the container holding device.

FIG. 5 is an explanatory drawing for describing the opening and closing operations of the container holding device 82 when a container (secondary sample container) before label sticking is received, label sticking is carried out, and the labeled container is transferred to the transfer mechanism 84. The horizontal axis shows the passage of time from t1 to t7, and the vertical axis shows the height position of the rollers 122, 124 from H1 to H7 on the line L—L.

At time t1, the container holding device 82 is positioned at the receiving position at the highest height H1, and with the container holding device 82 in a completely open state, the container 170 before label sticking is received from the manipulator 72. Accordingly, it is possible to cope with large-diameter containers. Namely, it is possible to handle containers having diameters up to the maximum diameter determined by the system.

When the container holding device 82 is lowered from the height H1, the container holding device 82 is gradually closed by the opening/closing control mechanism 88 in accordance with such lowering motion. For example, at time t2, the container holding device 82 is in a closed state at the height H3. In this way, because the container holding device 82 is gradually closed in accordance with such lowering motion, a large-diameter container is firmly held by the container holding device 82 at a higher position, and a small-diameter container is firmly held by the container holding device 82 at a lower position, and this makes it possible to cope with containers having a wide range of diameters. Namely, it is possible to carry out reliable holding of a container regardless of the diameter of the container.

At time t3, the container holding device 82 is lowered further and stopped at the container confirmation position at the height H4, and the confirmation of the presence or absence of a container is carried out by a reflection-type optical detector. Then, after the presence of the container has been confirmed, the container holding device 82 is lowered further, and at time t4, the container holding device 82 is positioned at the label sticking position at the lowest height H7, and at this position a label stored in the label sticking device 80 is stuck onto the container. Accordingly, it is possible to carry out label sticking for containers having various diameters.

After the label sticking operation has been completed, the container holding device 82 which holds the labeled container 170 is raised from the label sticking position, and at time t5, the container holding device 82 is stopped at the label confirmation position at the height H6. At this position, the confirmation as to whether there is a label stuck on the container is carried out by a transmission-type optical detector.

Then, the container holding device 82 is raised further, and at time t6, the container holding device 82 is positioned at the transfer position at the height H2, and when the container holding device 82 is partially opened, the container is transferred to the transfer mechanism 84. Specifically, the pair of container clamping members 154, 156 of the transfer mechanism 84 are closed to clamp the container inside the partially opened container holding device 82. Accordingly, instead of transferring the container when the container holding device 82 is in the normal completely open state, because the container is transferred when the container holding device 82 is in a partially opened state before complete opening regardless of the diameter of the container, there will be little or no rattling of the container inside the container holding device 82 at the time of transfer.

Next, at time t7, the container holding device 82 is lowered to the evacuation position at the height H5. In this state, the labeled container is separated from the container holding device 82, namely, the labeled container is held by the transfer mechanism 84. The height of the evacuation position can be established at an appropriate height that prevents the container holding device 82 from hindering the conveyance by the transfer mechanism 84. Then, the container holding device 82 is raised again and returns to the state of time t1.

When the container holding device 82 is raised and it is in the partially opened state at the transfer position at the height H2, the state of the gap between the container holding device 82 and the container is different depending on the diameter of the container. For example, when the container has a small diameter, the container is held in a half-opened state, but when the container has a large diameter, there is little or no gap. Even in this case, the opened state is different from a completely opened state, and therefore it is possible for the transfer mechanism 84 to receive the container from the container holding device 82 in a state where there is less rattling of the container.

The transfer position can be established in accordance with the diameter of the container to be transferred. For example, the diameter of the container can be detected with a container diameter sensor, and then the height of the transfer position of the container holding device 82 can be established by controlling the raising/lowering drive apparatus 102 in accordance with such data. When the diameter is known in advance, such data may be inputted into the control apparatus. Accordingly, it is possible to establish the proper state of the container holding device 82 at the container transfer time in accordance with the diameter of the container, whereby it becomes possible to smoothly transfer the container without rattling. In this case, because the height of the transfer position changes in accordance with the diameter of the container, the container clamping position of the transfer mechanism 84 and the container holding position of the manipulator 72 are adjusted as needed.

As described above, even though a so-called rear buffer was established as a buffer position for labeled containers, the present invention is not limited to this arrangement, and it is also possible to establish a so-called front buffer as a buffer position for containers before label sticking. Namely, a buffer position is provided for containers before label sticking, and a container holding device which can be opened and closed to hold a container receives a container before label sticking from a transfer mechanism at an upper receiving position of the raising/lowering path while in a completely opened state. Then, when the container holding device is lowered along the raising/lowering path by the raising/lowering mechanism, the container holding device is closed to hold the container by the opening/closing control mechanism in accordance with such lowering motion. Next, a label sticking operation is carried out at the label sticking position. Then, after the labeling sticking operation has been completed, the container holding device is raised, and the labeled container is received by the manipulator of the container conveying apparatus from the container holding device. Accordingly, the container conveying apparatus conveys the container before label sticking on the outward conveyance, and returns the labeled container on the return conveyance.

As described above, the sample pretreatment system according to the present invention has a simple structure which can handle containers having various diameters, and can efficiently carry out container conveyance and label sticking.

Finally, it is needless to mention that the present invention is not limited to the above-described embodiments but can be modified or improved in various ways within the scope described in claims.

What is claimed is:

1. A sample pretreatment system equipped with a pipetting apparatus for pipetting a sample to containers, a label sticking apparatus for sticking a label to each container, and a container conveying apparatus for conveying the containers, wherein the label sticking apparatus comprises:

a container holding device for holding the container with an elastic holding force, the holding device being adapted to open and close;

a raising/lowering mechanism for raising and lowering the container holding device along a raising/lowering path, the raising/lowering mechanism positioning the container holding device at a container receiving position which is set at an upper position when receiving the container, positioning the container holding device at a label sticking position by lowering the container holding device after receiving the container, and then raising the container holding device upwardly from the label sticking position after the label has been stuck on the container;

an opening/closing control mechanism for mechanically controlling opening and closing operations of the container holding device so that the container holding device is in a completely opened state at the receiving position and so that the container holding device carries out the closing operation according to the lowering motion of the container holding device from the receiving position to hold the container;

a label sticking apparatus for sticking a label onto the container held by the container holding device at the sticking position; and a transfer mechanism for receiving the container to which the label has been stuck from the container holding device which is raised after sticking the label and then conveying the container to which the label is stuck horizontally to position the labeled container at a buffer position; and wherein said container conveying apparatus is constructed so that the container conveying apparatus carries out feeding conveyance of a container before label sticking from the pipetting apparatus to the container holding device positioned at the receiving position in an outward conveyance and carries out returning conveyance of the container to which the label has been stuck and which is positioned at the buffer position to the pipetting apparatus in a returned conveyance.

2. The sample pretreatment system as claimed in claim 1, wherein the raising/lowering mechanism is operated to position the container holding device at the transfer position by raising the container holding device after the label has been stuck onto the container.

3. The sample pretreatment system as claimed in claim 2, wherein the transfer position is set depending on the diameter of the container to be transferred.

4. A sample pretreatment system equipped with a pipetting apparatus for pipetting a sample to containers, a label sticking apparatus for sticking a label to each container, and a container conveying apparatus for conveying the containers, wherein the label sticking apparatus comprises:

a container holding device for holding the container with an elastic holding force, the holding device being adapted to open and close;

a raising/lowering mechanism for raising and lowering the container holding device along a raising/lowering path, the raising/lowering mechanism positioning the container holding device at a container receiving position which is set at an upper position when receiving the container, positioning the container holding device at a label sticking position by lowering the container holding device after receiving the container, and then raising the container holding device upwardly from the label sticking position after the label has been stuck onto the container;

an opening/closing control mechanism for mechanically controlling opening and closing operations of the container holding device so that the container holding device is in a completely opened state at the receiving position and so that the container holding device carries out the closing operation according to the lowering motion of the container holding device from the receiving position to hold the container;

a label sticking apparatus for sticking a label onto the contain held by the container holding device at the sticking position; and a transfer mechanism for transferring the container before label sticking positioned at a buffer position to the container holding device at the receiving position by transferring the container horizontally; and wherein said container conveying apparatus is constructed so that the container conveying apparatus carries out feeding conveyance of a container before label sticking from the pipetting apparatus to the buffer position in an outward conveyance and carries out returning conveyance of the container by receiving the container to which the label has been stuck from the container holding device which has been raised after sticking the label.

* * * * *